US007371833B1

(12) United States Patent
Weiss

(10) Patent No.: US 7,371,833 B1
(45) Date of Patent: May 13, 2008

(54) NUCLEIC ACID MOLECULES WITH SPECIFIC RECOGNITION OF NATIVE PRP$^{SC}$, PRODUCTION AND USE

(76) Inventor: Stefan Weiss, Elisabethstr. 30, 80796 Munich (DE)

( * ) Notice: Subject to any disclaimer, the term of this patent is extended or adjusted under 35 U.S.C. 154(b) by 677 days.

(21) Appl. No.: 09/744,934

(22) PCT Filed: May 31, 2000

(86) PCT No.: PCT/EP00/05020

§ 371 (c)(1),
(2), (4) Date: Mar. 12, 2001

(87) PCT Pub. No.: WO00/73501

PCT Pub. Date: Dec. 7, 2000

(30) Foreign Application Priority Data

Jun. 1, 1999 (DE) ................................ 199 25 073

(51) Int. Cl.
*C07H 21/04* (2006.01)
*C12P 19/34* (2006.01)
*C12Q 1/68* (2006.01)

(52) U.S. Cl. ......................... 536/23.1; 436/6; 436/91.1

(58) Field of Classification Search ..................... None
See application file for complete search history.

(56) References Cited

FOREIGN PATENT DOCUMENTS

| | | |
|---|---|---|
| WO | WO 97/10505 | 3/1997 |
| WO | WO 9715685 A1 * | 5/1997 |
| WO | WO 98/35236 | 8/1998 |
| WO | WO 98/53838 | 12/1998 |

OTHER PUBLICATIONS

Agrawal et al. Antisense therapeutics: is it as simple as complementary base recognition? 2000 Mol. Med. Today: Reviews. vol. 61, pp. 72-81.*
Opalinska et al. Nucleic acid therapeutics: basic principlese and recent applications. 2002 Nature Reviews: Drug Discovery vol. 1, pp. 503-514.*
Jen et al. Suppression of gene expression by targeted disruption of messenger RNA: available options and current strategies 2000 Stem Cells vol. 18, pp. 307-319.*
Weiss, S. et al: "RNA Aptamers Specifically Interact With The Prion Protein PrP"; Journal Of Virology, vol. 71, No. 11, pp. 8790-8797 (Nov. 1997).
Demaimay, R. et al: "Late Treatment With Polyene Antibiotics Can Prolong The Survival Time Of Scrapie-Infected Animals"; J. Virol., vol. 71, pp. 9685-9689 (Dec. 1997).
Famulok, M.: "Molecular Recognition Of Amino Acids By RNA-Aptamers: An L-Citrulline Binding RNA Motif And Its Evolution Into An L-Arginine Binder"; J. Am. Chem. Soc., 116, pp. 1698-1706 (1994).
Gerhart, E., Wagner, H., Brantl, S.: "Kissing And RNA Stability In Antisense Control Of Plasmid Replication"; Trends Biochem. Sci., 23 (12), pp. 451-454 (Dec. 1998).
Korth, C., Stierli, B., Streit, P., Moser, M., Schaller, O., Fischer, R., Schulz-Schaeffer, W., Kretzschmar, H., Raeber, A., Braun, U., Ehrensperger, F., Hornemann, S., Glockshuber, R., Riek, R., Billeter, M., Wuthrich, K., Oesch, B.: "Prion (PrP$^{Sc}$)-Specific Epitope Defined By A Monoclonal Antibody"; Nature, vol. 390, pp. 74-77 (Nov. 6, 1997).
King, D. J. et al.: "Novel Combinatorial Selection Of Phosphorothioate Oligonucleotide Aptamers"; Biochemistry, 37, pp. 16489-16493 (1998).
Kumar, M., Carmichael, G. G.: "Antisense RNA: Function And Fate Of Duplex RNA In Cells Of Higher Eukaryotes"; Microbiol. Mol. Bio. Rev., vol. 62, No. 4, pp. 1415-1434 (Dec. 1998).
Lasmézas, C. I. et al.: "Transmission of the BSE Agent To Mice In The Absence Of Detectable Abnormal Prion Protein"; Science, vol. 275, pp. 402-405 (Jan. 17, 1997).
Lasmézas, C. I., Weiss, S.: "Molecular Biology Of Prion Diseases"; Cary, J. W., Linz, J. E., Bhatnagar, D., eds.; Microbial Foodborne Diseases: Mechanisms Of Pathogenesis And Toxin Synthesis, Technomic Publishing Co., Lancaster, Pennsylvania, pp. 495-537, 1999/2000.
Prusiner, S. B., Scott, M. R., DeArmond, S. J., Cohen, F. E.: "Prion Protein Biology"; Cell, vol. 93, pp. 337-348 (May 1, 1998).
Rieger, R. Lasmézas, C. I. Weiss, S.: "Role Of The 37kDa Laminin Receptor Precursor In The Life Cycle Of Prions"; Transfus Clin. Biol., 6, pp. 7-16 (1999).
Scott, M. R., Kohler, R., Foster, D., Prusiner, S. B.: "Chimeric Prion Protein Expression In Cultured Cells And Transgenic Mice"; Protein Science, 1, pp. 986-997 (1992).
Tuerk, C., Gold, L.: "Systematic Evolution Of Ligands By Exponential Enrichment: RNA Ligands To Bacteriophage T4 DNA Polymerase"; Science, vol. 249, pp. 505-510 (Aug. 1990).
Vanhée-Brossollet, c., Vaquero, C.: "Do Natural Antisense Transcripts Make Sense In Eukaryotes?"; Gene, 221 (1), pp. 1-9 (1998).

Weissmann, C., Aguzzi, A: "Bovine Spongiform Encephalophathy And Early Onset Variant Creutzfeldt-Jakob Disease"; Curr. Opin. Neurobiol., 7, pp. 695-700 (1997).

* cited by examiner

*Primary Examiner*—Tracy Vivlemore
(74) *Attorney, Agent, or Firm*—Breiner & Breiner, LLC

(57) ABSTRACT

The invention relates to a method for isolating nucleic acid molecules which are capable of specific interaction with native PrP$^{Sc}$ and can differentiate between native PrP$^{c}$ and native PrP$^{Sc}$. The inventive method comprises the following steps: incubating a pool of nucleic acids with purified PrP$^{Sc}$ preparations (PPPs); selecting and isolating the resulting protein/nucleic acid complexes and optionally amplifying the specific nucleic acids, in addition to optionally repeating the incubation and isolation stage. The invention also relates to the nucleic acid molecule produced by this method and the use thereof for diagnosing and treating transmissible spongiform encephalopathies.

2 Claims, 8 Drawing Sheets

SEQUENCE LISTING

```
<160> NUMBER OF SEQ ID NOS: 6

<210> SEQ ID NO 1
<211> LENGTH: 73
<212> TYPE: RNA
<213> ORGANISM: Artificial Sequence
<220> FEATURE:
<223> OTHER INFORMATION: Description of artificial sequence: nucleic
      acid molecule specifically binding to native PrPsc, selected from
      RNA pool M111.1 (M. Famulok, J. Am. Chem. Soc. 116 (1994) 1698)

<400> SEQUENCE: 1
ggcaaaggcg ggaaagcgug cuaacgugga aagcuacucc cacguuguac gcgucgcaga      60
ucauugagug agg                                                         73

<210> SEQ ID NO 2
<211> LENGTH: 112
```

```
<212> TYPE: RNA
<213> ORGANISM: Artificial Sequence
<220> FEATURE:
<223> OTHER INFORMATION: Description of artificial sequence: nucleic
      acid molecule specifically binding to native PrPsc, selected from
      RNA pool M111.1 (M. Famulok, J. Am. Chem. Soc. 116 (1994) 1698)

<400> SEQUENCE: 2
ggagcucagc cuucacugcg gcaaaggcgg gaaagcgugc uaacguggaa agcuacuccc      60
acguuguacg cgucgcagau cauugaguga ggggcaccac ggucggaucc uc             112

<210> SEQ ID NO 3
<211> LENGTH: 73
<212> TYPE: RNA
<213> ORGANISM: Artificial Sequence
<220> FEATURE:
<223> OTHER INFORMATION: Description of artificial sequence: nucleic
      acid molecule as a control for specific binding of native PrPsc,
      selected from RNA pool M111.1 (M. Famulok, J. Am. Chem. Soc. 116
      (1994) 1698)

<400> SEQUENCE: 3
uccaggccga gugcaggaug uaaucgaguc caucugauug cuaauagauu ccucauucau      60
cagcacauau agc                                                         73

<210> SEQ ID NO 4
<211> LENGTH: 113
<212> TYPE: RNA
<213> ORGANISM: Artificial Sequence
<220> FEATURE:
<223> OTHER INFORMATION: Description of artificial sequence: nucleic
      acid molecule as a control for specific binding to native PrPsc,
      selected from RNA pool M111.1 (M. Famulok, J. Am. Chem. Soc. 116
      (1994) 1698)

<400> SEQUENCE: 4
ggagcucagc cuucacugcg uccaggccga gugcaggaug uaaucgaguc caucugauug      60
cuaauagauu ccucauucau cagcacauau agcggcacca cggucggauc cuc            113

<210> SEQ ID NO 5
<211> LENGTH: 44
<212> TYPE: DNA
<213> ORGANISM: Artificial Sequence
<220> FEATURE:
<223> OTHER INFORMATION: PCR Primer I

<400> SEQUENCE: 5
ccgaattcta atacgactca ctataggagc tcagccttca ctgc                       44

<210> SEQ ID NO 6
<211> LENGTH: 20
<212> TYPE: DNA
<213> ORGANISM: Artificial Sequence
<220> FEATURE:
<223> OTHER INFORMATION: PCR Primer II

<400> SEQUENCE: 6
gtggatccga ccgtggtgcc                                                  20
```

NUCLEIC ACID MOLECULES WITH SPECIFIC RECOGNITION OF NATIVE PrP$^{SC}$, PRODUCTION AND USE

RELATED APPLICATION

This application hereby claims benefit under 35 U.S.C. § 365(a) of PCT Application No. PCT/EP00/05020, filed May 31, 2000, entitled "Nucleic Acid Molecules With Specific Identification Of Native PrP$^{Sc}$, Their Production And The Use Thereof", and claims benefit under 35 U.S.C. § 119 of German Application No. 199 25 073, filed Jun. 1, 1999, entitled "Nucleic Acid Molecules With Specific Identification Of Native PrP$^{Sc}$, Their Production And The Use Thereof".

The present invention lies within the area of nucleic acids and their derivatives which are able to interact with prion proteins which are involved in the occurrence of very diverse forms of transmissible spongiform encephalopathy (TSE). In particular, the present invention relates to a method for the selection and isolation of nucleic acid molecules which are able to distinguish specifically between the PrP$^c$ and PrP$^{Sc}$ isoforms, to nucleic acid molecules obtainable by this method and to pharmaceutical and diagnostic compositions which comprise these nucleic acid molecules.

Prions, the presumed cause of transmissible spongiform encephalopathies (TSE) such as scrapie in sheep, mice and hamsters, bovine transmissible spongiform encephalopathy (BSE), transmissible spongiform mink encephalopathy (TME), kuru, Gerstmann-Sträußer-Scheinker syndrome (GSS), Creutzfeldt-Jakob disease (CJD) and fatal familial insomnia (FFI) in humans, consist principally, if not entirely, of PrP$^{Sc}$, an abnormal isoform of the ubiquitous cellular prion protein PrP$^c$ (for overview: Lasmézas and Weiss, 1999; Rieger et al., 1999; Prusiner et al., 1998; Weissmann and Aguzzi, 1997).

WO 97/15685 and the references cited therein disclose that, of the PrP$^c$ and PrP$^{Sc}$ isoforms, only PrP$^{Sc}$ can be processed to the isoform PrP27-30 which is resistant to proteinase K. PrP$^{Sc}$ differs from PrP$^c$ in respect of the secondary structure, i.e. the proportion of α-helix and β-pleated sheet structures. It is also known that, in the case of the Syrian Golden Hamster, PrP27-30 is truncated by 67 amino acids at the amino terminus by comparison with PrP$^c$ and PrP$^{Sc}$.

This property was used in WO 97/15685 for the diagnosis of diseases associated with prion proteins. According to the teaching of WO 97/15685, PrP$^c$ fused to GST was employed in a test for identifying and selecting specific nucleic acid sequences intended to be capable of distinguishing of [sic] between the cellular isoforms PrP$^c$ and PrP$^{Sc}$. PrP$^c$ and recombinant (rec) PrP27-30, which was—as mentioned above—a PrP$^c$ from the Syrian Golden Hamster merely truncated by 67 amino acids at the amino terminus, were employed as glutathione S-transferase (GST) fusions in order to examine the binding properties of the selected nucleic acid molecules.

The process described in WO 97/15685 for the identification and isolation of specific nucleic acid molecules comprised in this connection the following steps:

incubating PrP$^c$ fused to glutathione S-transferase (GST) with a pool of nucleic acid molecules comprising different sequences, selecting and isolating the nucleic acid molecules which are capable of binding to PrP$^c$ fused to GST, optionally amplifying the isolated nucleic acid molecules, optionally repeating the incubation step and the selection step, and determining the binding specificity of the isolated nucleic acid molecules for the isoforms PrP$^c$ and PrP$^{Sc}$ or PrP27-30 or the fragments or derivatives thereof.

The fact that the nucleic acid molecules found in the selection do not bind to recPrP27-30 merely demonstrates, however, the binding of the nucleic acid molecule to the amino-terminal region of the PrP$^c$ molecule.

On the contrary, it has emerged that it was impossible to obtain by the process described in WO 97/15685 nucleic acid molecules binding specifically only to native PrP$^{Sc}$. Furthermore, a PrP$^c$-specific nucleic acid molecule detected in WO 97/15685 cannot be employed for the direct diagnosis of transmissible spongiform encephalopathies (TSE).

It is an object of the present invention therefore to provide nucleic acid molecules which specifically bind to PrP$^{Sc}$ in the native state and are capable of distinguishing it from PrP$^c$.

The first aspect of the present invention accordingly relates to a method for the selection and isolation of nucleic acid molecules which are capable of specific interaction with native PrP$^{Sc}$ and of distinguishing native PrP$^c$ and native PrP$^{Sc}$, where the method comprises the following steps:

incubating a pool of nucleic acids having different sequences with purified PrP$^{Sc}$ preparations (PPPs), selecting and isolating the resulting protein/nucleic acid complexes, and optionally amplifying the isolated specific nucleic acids, and optionally repeating the incubation, isolation and amplification steps.

The above method preferably also comprises an identification of the resulting nucleic acid molecules in a manner known per se.

By the term "pool of nucleic acids" we mean any mixture of nucleic acid molecules comprising different sequences, preferably a pool of highly degenerate nucleic acids of great complexity. It is particularly preferred for this pool to be the RNA pool M111.1 known in the relevant art (Famulok, 1994). In another preferred embodiment, this pool is a randomized DNA/RNA pool where the DNA/RNA molecules are modified so that they have increased stability.

By the term "purified PrP$^{Sc}$ preparations (PPPs)" we mean PrP$^{Sc}$ preparations which have been obtained by a special processing method without the use of proteinase K (PK) in accordance with the description given below.

In this connection, PrP$^{Sc}$ is isolated in the form of a pellet from tissues from animals suffering from a transmissible spongiform encephalopathy in the clinical step by the method described in the experimental part of the description for the example of TSE and brain homogenate.

It is possible to use according to the invention as nucleic acid molecules single- or double-stranded nucleic acid molecules such as RNA, modified RNA, single-stranded DNA or double-stranded DNA.

The term "native PrP$^c$" comprises according to the invention the ubiquitous cellular isoform of the prion protein, and fragments and derivatives thereof, irrespective of the organism from which they originate.

The term "native PrP$^{Sc}$" comprises the abnormal isoform, which is associated with transmissible spongiform encephalopathies, of the prion protein, and naturally occurring derivatives thereof, irrespective of the organism from which they originate.

By the term "native" we mean in its broadest form present under non-denaturing conditions, where denaturing conditions are to be regarded as conditions destroying the conformation of the biomolecule.

The term "derivative" comprises in its most general form chemically modified versions of the isoforms of the PrP$^c$ and PrP$^{Sc}$ prion proteins, and mutants of these proteins, i.e. proteins which differ from the naturally occurring prion protein isoforms in one or more positions of the amino acid sequence, and proteins which have deletions and/or insertions by comparison with the naturally occurring prion protein isoforms. Mutants of these types may have been produced by recombinant DNA technology or may be naturally occurring mutants. The term derivatives also comprises proteins which contain modified amino acids, or proteins which are modified by glycosylation, phosphorylation or the like.

The purified PrP$^{Sc}$ preparations (PPPs) which are used according to the invention as probe or target for isolating nucleic acid molecules which are capable of specific interaction with native PrP$^{Sc}$ and of distinguishing native PrP$^c$ and native PrP$^{Sc}$, which represent as infectious fraction mainly an aggregated form of PrP$^{Sc}$ can be isolated in the form of a pellet for example from scrapie-infected hamster brains without treatment with proteinase K.

It is possible by the method of the invention to isolate nucleic acid molecules able to distinguish between a native ubiquitous PrP$^c$ and the native abnormal isoform PrP$^{Sc}$, which are associated with the abovementioned transmissible spongiform encephalo-pathies such as scrapie in sheep, mice and hamsters, bovine spongiform encephalopathy of cattle (BSE), transmissible mink encephalopathy in mink (TME), kuru, Gerstmann-Sträßler-Scheinker syndrome (GSS), Creutzfeldt-Jakob disease (CJD) including the new variant (nvCJD) and fatal familial insomnia (FFI) in humans, chronic wasting disease (CWD) in mule, deer and elk and feline transmissible spongiform encephalopathy (FSE).

Incubation of the nucleic acid pool with PPPs can take place in various ways.

In a preferred embodiment, the PPPs in pellet form are taken up in a suitable suspending agent, for example binding buffer, and incubated with the nucleic acid pool to form a colloidal solution.

The PPPs can, however, also be immobilized on a matrix, for example a gel or a resin. The immobilization in this case takes place in a manner known per se to the skilled worker in the relevant art. For example, the PPPs can be covalently bonded to the matrix or be bound to the matrix by a specific interaction between a group present on the matrix and a domain in the proteins of the PPPs which specifically recognizes the group on the matrix. Such a domain can be fused to the PPP precursor molecules in a manner known to the skilled worker in the relevant art, for example within the framework of recombinant DNA techniques.

It is possible within the framework of a preferred embodiment of the method of the invention to carry out a preselection to remove non-specifically binding nucleic acid molecules. This can take place, for example, using "pseudo PPPs" which have been obtained from scrapie-uninfected brain homogenates. This preselection can take place according to the invention, as described above for the incubation with the PPPs, using "pseudo PPPs" in colloidal solution or in a form immobilized on a matrix.

The resulting protein/nucleic acid complexes can be isolated in a manner known in the relevant art. For example, in the case of immobilized PPPs, unbound nucleic acid molecules can be washed out with a suitable buffer after the incubation. It is then possible for the bound nucleic acid molecules to be eluted, for example with 8M urea, and be further purified subsequently by phenol extraction and precipitation. In the case of incubation with PPPs in colloidal solution, the complexes formed can be obtained by ultracentrifugation in a pellet from which the nucleic acid molecules can be extracted. An alternative possibility is to filter the complexes formed after incubation of the nucleic acid molecules with the PPPs.

A further possibility according to the invention is to amplify the resulting nucleic acid molecules where appropriate, for example by in vitro transcription, reverse transcription or PCR or a combination of these techniques, and then to subject the resulting products to the incubation and isolation (=selection) steps once more. It is possible by such a repetition of incubation, isolation and amplification steps to concentrate the specifically binding nucleic acid molecules.

Thus, for example, amplification can result in a concentration of <0.01% nucleic acid products in a first cycle, of 5% in the second and of >30% in the third, in the RNA pool directed against PPPs (i.e. in the first cycle <0.01% of the nucleic acid molecules in the RNA pool bind specifically to the PPPs, 5% bind in the second cycle and >30% bind in the third cycle).

In a preferred embodiment of the present invention, the nucleic acid molecules obtained by selection and isolation are identified in a manner known per se to the skilled worker.

A further aspect of the present invention relates to nucleic acid molecules which are obtainable by the above method and which bind specifically to native PrP$^{Sc}$ and are capable of distinguishing native PrP$^c$ and native PrP$^{Sc}$. The term nucleic acid molecules in this connection comprises according to the invention RNA, antisense RNA, single-stranded and double-stranded DNA, which bind specifically to native PrP$^{Sc}$ and are capable of distinguishing native PrP$^c$ and native PrP$^{Sc}$.

In a preferred embodiment, the nucleic acid molecules comprise the following nucleotide sequence at the RNA level:

[SEQ ID NO: 2]

5'ggagcucagc cuucacugcg gcaaaggcgg gaaagcgugc uaacguggaa 50
agcuacuccc acguuguacg cgucgcagau cauugaguga ggggcaccac 100
ggucggaucc uc3' 112

In a further preferred embodiment, the nucleic acid molecules comprise the following nucleotide sequence at the RNA level:

[SEQ ID NO: 1]

5'ggcaaaggcg ggaaagcgug cuaacgugga aagcuacucc cacguuguac 50
gcgucgcaga ucauugagug agg3' 73

In a further embodiment of the present invention, the nucleic acid molecules are modified further at one or more positions in order to increase the stability and/or in order to alter their biochemical and/or biophysical properties. The scope of the present invention includes in this connection in particular the following manipulations:

A. To increase the in vitro/in vivo stability of the nucleic acid molecules of the invention and/or their resistance to nucleases:
complete or partial replacement of the phosphate backbone by a phosphorothioate backbone;
complete or partial replacement of the nucleotide loops by non-nucleotide spacer groups (for example hexaethylene glycol);
complete or partial replacement of nucleotides by 2'-aminopropyl- or 2'-amino- or 2'-O-alkyl- or 2'-fluororibonucleotides;

substitution of the pyrimidine base in position 5 by 1-pentenyl radicals;

cappings with modified nucleotides (for example phosphorothioates or inverted 3'-3' nucleotides);

stabilization with the aid of crosslinking disulfide bonds;

inclusion of chiral counterparts;

addition of lipid groups and incorporation of the aptamer derivatized with lipid groups in liposomes;

coupling to biopolymer carriers such as, for example, polyethylene glycol;

encapsulation of the nucleic acid molecules.

B. To improve the affinity and/or activity of the nucleic acid molecules:

modification of the RNA to produce an aptamer which can be crosslinked by exposure to radiation, for example by incorporation of 5-iodouridine triphosphate;

coupling of RNA to a small organic ligand which recognizes another region of the target molecule and itself takes part in the reaction.

C. To improve the detectability in diagnostic tests:

labeling with a fluorophore;

labeling with digoxigenin;

labeling with biotin.

The nucleic acid molecule described above as preferred according to the invention and having the formula indicated above is a nucleic acid molecule which is able to form a stem/loop structure and which specifically reacts with native proteinase K-untreated $PrP^{Sc}$ but not with PrP27-30, the stable $PrP^{Sc}$ form resulting from proteinase K digestion, and with native authentic $PrP^{c}$. The prion preparations may moreover originate, for example, from hamster, mouse, cattle or humans. This nucleic acid molecule which binds specifically to native $PrP^{Sc}$ is frequently also referred to in the literature (cf., for example, WO 97/15685 and the references indicated therein, and Tuerk and Gold, 1990) as RNA aptamer.

However, the aptamer of the invention reacts, for example, with denatured $PrP^{c}$ and $PrP^{Sc}$ from hamsters, cattle ($PrP^{BSE}$), humans ($PrP^{CJD}$) and mice, which demonstrates the specific recognition of only native $PrP^{Sc}$.

Evidence that the RNA aptamers of the invention specifically bound to the prion proteins $PrP^{Sc}$ but not to $PrP^{c}$ and the stable PrP27-30 resulting from proteinase K digestion was provided, for example, by North-Western blot analysis with brain homogenates from uninfected hamsters and hamsters suffering from scrapie in the terminal step, with and without proteinase K. Under native conditions, for example, RNA aptamers selected after the third cycle bound specifically to $PrP^{Sc}$ (FIG. 1*a*) but not to $PrP^{c}$ and PrP27-30.

In contrast thereto, the polyclonal antibody JB007 recognized $PrP^{c}$, $PrP^{Sc}$ and PrP27-30 (FIG. 1*b*), which demonstrates the specific binding of the RNA aptamers to $PrP^{Sc}$. Under denaturing conditions, the aptamer of the invention recognized $PrP^{c}$ and $PrP^{Sc}$ (FIG. 1*c*), but did not react with PrP27-30. The monoclonal antibody 3F4 recognized $PrP^{c}$, $PrP^{Sc}$ and PrP27-30 (FIG. 1*d*).

Another preferred embodiment of the present invention relates to an antisense RNA of a nucleic acid molecule obtainable by the method of the invention. The term "antisense RNA" has in this connection the meaning generally known in the relevant art (cf. Kumar and Carmichael, 1998, Gerhart et al. 1998 and Vanhee-Brossollet and Vaquer, 1998).

A further aspect of the present invention relates to a method for investigating the ability of macromolecules such as nucleic acid molecules or antibodies to bind selectively to $PrP^{Sc}$ under native conditions, the method comprising the following steps:

sonication of the tissue sample in order to produce a clear solution of the tissue sample, separation of the clear solution by native polyacrylamide electrophoresis (preferably using a PAA gradient (usually 3.5 to 12% PAA, preferably 4 to 12% PAA and, in particular, 6 to 12% PAA)) in order to obtain single protein bands, and subsequent electroblotting and subsequent detection of native $PrP^{Sc}$, preferably either by means of North-Western blotting by detecting nucleic acids selectively binding to native $PrP^{Sc}$, or by means of Western blotting by detecting native $PrP^{Sc}$ by means of an antibody (e.g. JB 007, SAF 32, 15 B3).

Alternatively, the clear solution can be separated by native agarose gel electrophoresis (preferably using an agarose gradient).

A further aspect of the present invention relates to the use of the nucleic acid molecules of the invention as defined above as means for diagnosing transmissible spongiform encephalopathies (TSE).

As can be established according to the invention, for example by North-Western blotting or the dot-blot technique, the nucleic acid molecules of the invention are able selectively to recognize, for example, native hamster, murine, human and bovine $PrP^{Sc/CJD/BSE}$.

In contrast thereto, the recPrP-I aptamer (corresponds to RNA aptamer motif I (Ap 1) in Weiss et al., 1997) and PrP antibodies were able to recognize both native $PrP^{c}$ and $PrP^{Sc}$. Under denaturing conditions, however, the nucleic acid molecules of the invention and the recPrP-I aptamers react both with $PrP^{c}$ and hamster, murine, human and bovine $PrP^{Sc/CJD/BSE}$, which demostrates the specific recognition of $PrP^{Sc/CJD/BSE}$ only in the native state.

A further aspect of the present invention further relates to diagnostic compositions comprising the nucleic acid molecules of the invention. Compositions of this type may furthermore comprise conventional excipients known in the relevant art for use in compositions of this type. The diagnostic compositions of the invention are suitable for carrying out a diagnostic test for detecting prion diseases in various animal species and in humans. Thus, the diagnostic compositions of the invention can be used in methods for diagnosing the abovementioned transmissible spongiform encephalopathies. Such a method may comprise, for example, the incubation of a sample taken from the body of the species to be investigated with a nucleic acid molecule of the invention and a subsequent determination of the interaction of the nucleic acid molecules with native $PrP^{Sc}$. It is possible in this connection to employ the nucleic acid molecules of the invention in a specific and simple method without the need for a previous digestion with proteinase K of the native material. Determination of the interaction of the nucleic acid molecules with native $PrP^{Sc}$ can in this case take place for example by measuring the ligand-bound radioactivity, by means of fluorometric determination with the aid of a biosensor or with the use of a suitably adapted enzyme-linked oligonucleotide assay (ELOA) technique. It is also possible according to the invention to determine the amount of native $PrP^{Sc}$ in a sample quantitatively by measuring the radioactivity, fluorescence anisotropy or by densitometric measurement with the aid of an ELOA test.

In a preferred embodiment, the sample to be investigated may originate from a wide variety of organs and tissues, for example fixed in formalin or in frozen form, for example from brain, tonsils, intestine, dura mater, lymph nodes, nerves, spleen, placenta, stomach, eyes, spinal cord or Peyer's patches. The samples may also comprise body fluids, preferably blood, cerebrospinal fluid, milk or sperm.

Where brain is to be used as sample, the diagnosis is usually carried out post mortem. However, it is also possible to carry out the diagnostic investigation in the form of brain biopsies on the living organism. Investigations of the above-mentioned body fluids and of organ samples can likewise be carried out on the living organism.

A further aspect of the present invention relates to pharmaceutical compositions which comprise the nucleic acid molecules of the invention. Compositions of this type may additionally comprise pharmaceutically acceptable carriers and other excipients known in the relevant art. Particularly suitable excipients are those which increase the in vivo half-life of the nucleic acid molecules of the invention or improve a specific binding of the nucleic acid molecules of the invention.

Specific examples of such excipients are the substances mentioned above in connection with increasing the stability and/or altering the biochemical and/or biophysical properties of the nucleic acid molecules of the invention. It is also possible for the nucleic acid molecules of the invention to be encapsulated in conventional materials or incorporated in liposomes in the manner known to the skilled worker in the relevant art.

These pharmaceutical compositions of the invention are suitable for treatment of the transmissible spongiform encephalopathies described above. Thus, for example, the production of PrP sc in infected cells can be suppressed by oral or parenteral (for example intravenous) administration of the pharmaceutical compositions of the invention.

Thus, according to the invention, for example scrapie-infected neuroblastoma cells [ScN$_2$a (MHM-2)] were transfected with the RNA transcription plasmids pCIneo (mock), pCIneo_PPP-I and pCIneo_recPrP-I. This transgenic cell type contains a chimeric mouse/hamster/mouse PrP construct, so that it is possible to distinguish between endogenously expressed mouse PrP and transgenically expressed hamster PrP with the aid of specific antibodies, such as 3F4 which does recognize hamster PrP but not mouse PrP. Western blot analysis of protein preparations of these cells 48 h after transfection revealed, after proteinase K (pK) treatment, that cells transfected with pCIneo_PPP-I, which produces the PPP-I aptamer (112-mer; SEQ ID No. 2), did not produce PrP$^{Sc}$ (FIG. 7a, lane 2). In contrast thereto, the aptamer recPrP-I (cf. RNA aptamer motif I (Ap 1) Weiss et al., 1997) had no effect on the production of PrP$^{Sc}$ (FIG. 7a, lane 3), just like the mock control wherein transfection was done with the vector pCIneo (FIG. 7a, lane 1).

To analyze the levels of PPP-I RNA and recPrP-I RNA in the neuroblastoma cells [(ScN$_2$a (MHM-2)] which were transfected with pCIneo (FIG. 7b, mock, lane 1), pCIneo_PPP-I (FIG. 7b, lane 2) and pCIneo_recPrP-I (FIG. 7b, lane 3), the total RNA was purified at the same time as the production of the protein preparations. After reverse transcription of this RNA with PCR primer I and PCR amplification of the cDNA with PCR primers I and II, analysis by agarose gel electrophoresis showed that the cells transfected with pCIneo_PPP-I and pCIneo_recPrP-I produced the same levels of PPP-I RNA (112-mer; SEQ ID No. 2) (FIG. 7b, lane 2) and recPrP-I RNA (FIG. 7b, lane 3), whereas the cells transfected with pCIneo (mock) showed no levels of PPP-I RNA and recPrP-I RNA (FIG. 7b, lane 1).

These data show that transcription of PPP-I RNA in ScN$_2$a cells reduces the PrP$^{Sc}$ level and the PrP$^c$ level (data not shown) below the detection limit. This effect is moreover attributable not to an increased level of transcription of PPP-I RNA compared with recPrP-I RNA, but to the PPP-I RNA property of suppressing PrP$^{Sc}$/PrP$^c$ expression.

These data suggest that the PPP-I aptamer is heavily involved in the process of forming native PrP$^{Sc}$ in vivo through specific interaction with native PrP$^{Sc}$ and presumably also with early PrP synthesis intermediates. The aptamer may also be involved in the metabolism of PrP$^c$. This is the origin of the usability of the aptamer of the invention as means for treating TSE.

Since the PPI-I aptamer is demonstrably able to "capture" PrP$^{Sc}$ molecules, it may also be referred to as an RNA decoy or PPI-I decoy. DNA decoys are described in the literature, for example by King et al., 1998.

The interaction of the nucleic acid sequences of the invention under denaturing conditions with both PrP$^c$ and PrP$^{Sc}$, and the lack of interaction with PrP27-30, which lacks 67 to 76 amino acids, depending on the species, at the amino-terminal end compared with PrP$^{Sc}$, suggest that recognition takes place at an epitope in the amino-terminal part of PrP$^{Sc}$ (AA23/25 to 90-101). The finding that four species, humans, cattle, hamsters and mice (data not shown here), are recognized by the aptamer is in favor of the assumption that the recognition site in PrP which is recognized by the nucleic acid molecules of the invention is highly conserved in different mammals.

DESCRIPTION OF THE DRAWINGS

List of abbreviations:

1. Ab 3F4 = monoclonal antibody 3F4
2. Ab 15B3 = monoclonal antibody 15B3
3. Ab JB007 = polyclonal antibody JB007
4. Ab SAF32 = monoclonal antibody SAF32
5. Ap Ctrl-I = control aptamer (112-mer; SEQ ID No. 4)
6. Ap PPP-I = aptamer PPP-I (112-mer; SEQ ID No. 2)
7. Ap recPrP-I = RNA aptamer motif I (Ap1) (cf. Weiss et al., 1997)
8. BSE = brain homogenate from a bovine with BSE
9. CJD = brain homogenate from a patient suffering from sporadic CJD
10. Sc = brain homogenate from a hamster with scrapie
11. M$_r$(b) = molecular weight standard in bases
12. M$_r$(K) = molecular weight standard in kDa
13. N = normal brain homogenate from hamster (FIGS. 1, 3, 4, 5) or human and bovine (FIG. 6)
14. PK = proteinase K
15. -pk = without proteinase K digestion
16. +pk = with proteinase K digestion
17. Pool RNA = randomized RNA pool (Famulok; 1994)
18. PPP = purified PrP$^{Sc}$ preparation
19. PrP27-30 = proteinase-resistant prion protein.

FIGS. 1a, b, lanes 3) demonstrates that the PPP aptamers are able to recognize native PrP$^{Sc}$ specifically.

Figure 1:
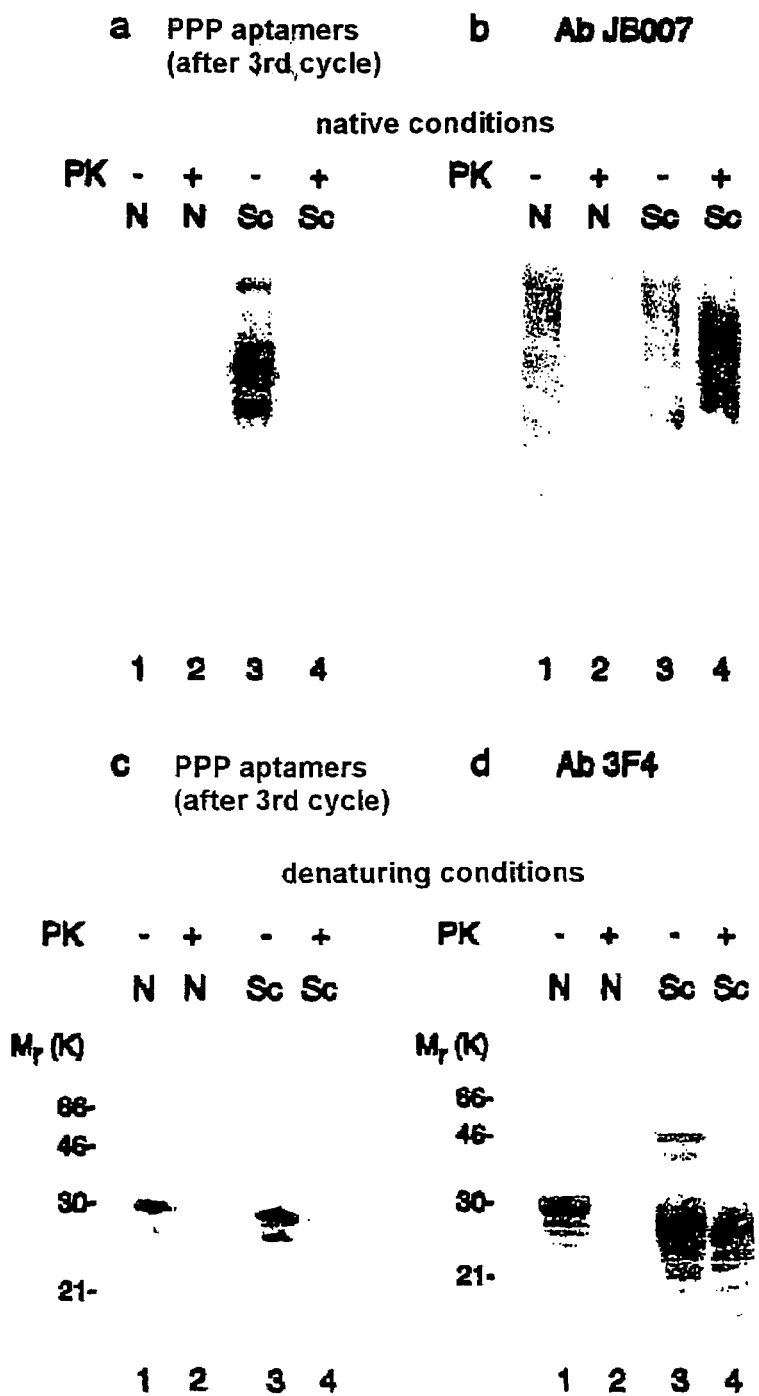
FIG. 1 shows the North-Western and Western blot analyses of brain homogenates from uninfected hamsters and hamsters suffering from scrapie with PPP aptamers (after the 3rd cycle) and PrP-specific antibodies under native and denaturing conditions. Brain homogenates from uninfected hamsters without (lanes 1) and with pK (lanes 2) and brain homogenates from hamsters suffering from scrapie without (lanes 3) and with pK (lanes 4) were fractionated on native PAA gradient gels, 6-12% (a, b) and denaturing SDS-12% PAA gels (c, d), blotted and developed with radiolabeled PPP aptamers (after the 3rd cycle) (a, c) and the antibodies JB007 (b) and 3F4 (d). The fact that the JB007 antibody recognizes the same protein bands as the PPP aptamers (cf.

The present invention is explained in detail hereinafter with reference to the drawings on the basis of examples which do not have a restrictive effect.

EXAMPLES

Example 1

Production of the $PrP^{Sc}$-Specific PPP-I Aptamer
Materials

Preparation of the PPPs

PPPs were produced for example from brains from rodents, for example hamsters, inoculated intra-cerebrally with scrapie, in the terminal clinical step, in a known manner (Lasmezas et al., 1997) or by the method described hereinafter, no digestion with proteinase K being carried out. The "pseudo" PPPs were produced by an analogous method from uninfected hamster brains, but no digestion with proteinase K was carried out in any case.

Before the in vitro selection, the PPPs and "pseudo" PPPs were washed once with 300 µl of binding buffer (Weiss et al., 1997) consisting of 8 mM $Na_2HPO_4$; 0.87 mM $KH_2PO_4$; 136 mM NaCl; 112.6 mM KCl; 2 mM DTT; 2 mM $MgCl_2$.

Preparation of Brain Homogenates

Brain homogenates were prepared from uninfected hamsters, hamsters inoculated intracerebrally with the scrapie strain 263K, uninfected mice; mice inoculated with the scrapie strain C506 M3, uninfected cattle, cattle suffering from BSE (from M. Dawson, C V L, G B), a person who died from a non-neurological disease, and a patient suffering from sporadic CJD.

Brain material was homogenized to produce a 20% (w/v) solution in a 5% isotonic glucose solution. Subsequently 200 µl of 20% NaCl and 200 µl of a freshly prepared solution of 20% sarcosyl, 2% SB3-14 and 2 mM tris buffer of pH 7.4 were added to 200 µl of 20% brain homogenate in isotonic glucose solution. After incubation at 37° C. for one hour, the mixture was placed on a sucrose cushion consisting of 10% NaCl, 20% sucrose, 0.1% SB3-14 and 10 mM tris buffer of pH 7.4 and centrifuged at 30 000 g at room temperature for 2 hours. The supernatant was discarded and the pellet was resuspended for example in binding buffer for further use.

RNA pool M111.1

The RNA pool 111.1 (randomized sequence: 74 nucleotides; base permutation $3.56 \times 10^{44}$; pool complexity $1.03 \times 10^{15}$ (Famulok, 1994)) which was described for the in vitro selection method against recombinant hamster $PrP^c$ (Weiss et al., 1997) was used.

Antibody

The antibody 3F4 was obtained from Senetek PLC. The polyclonal antibody JB007 was produced in a known manner (cf. Demaimay et al., 1997). The antibody SAF 32 was produced in the Service de Neurovirologie (CEA, Fontenay-aux-Roses, France) and Service de Pharmacologie et Immunologie (CEA, Saclay, France). It recognizes the AA 53-93 region of the prion protein. The monoclonal antibody 15 B3 originated from Bruno Oesch, Zurich and is described in Korth et al., 1997.

In-Vitro Selection Against PPPs

183 µg of radiolabeled [5'-γ-$^{32}$P-ATP] RNA 111.1 (Weiss et al., 1997), which was purified on Sephadex G50 columns, was incubated in a first preselection cycle with "pseudo PPPs" (taken up in phosphate binding buffer) isolated from 40 mg of uninfected hamster brain (Weiss et al., 1997) in the presence of 120 U of RNasin (Roche Diagnostics). After incubation at 37° C. in an overhead shaker for one hour and centrifugation at 15 000 rpm/min for 10 minutes, the supernatant was incubated with PPPs prepared from 40 mg of brain from hamsters suffering from scrapie. After ultracentrifugation (70 000×g, 30 min) and washing steps, the RNA was eluted from the PPP pellet with 8M urea, and the RNA was purified by phenol extraction and EtOH precipitation. The percentage binding of the RNA to the PPPs was determined by measuring the radioactivity (dpm) of the RNA pellet after the ethanol precipitation divided by the total amount (dpm) of RNA before the selection cycle. 50% of the RNA were then subjected to a reverse transcription reaction with the following PCR primer I, and 50% of the cDNA obtained thereby were amplified by PCR with the PCR primer I and the following PCR primer II.

PCR primer I comprises the following:

[SEQ ID NO: 5]

5'ccgaattcta atacgactca ctataggagc tcagccttca ctgc3' 44.

PCR primer II comprises the following:

[SEQ ID NO: 6]

5'gtggatccga ccgtggtgcc3' 20.

50% of the amplified cDNA were then transcribed in vitro using T7 RNA polymerase in the presence of [α-$^{32}$P-UTP]. The RNA obtained thereby was purified in a known manner (Weiss et al., 1997). This was done by fractionating the RNA on a 15% denaturing PAA gel, cutting the dominant RNA bands out of the gel and subsequently eluting and precipitating. 40 µg of the individual radiolabeled RNA were subjected to a second and third cycle of selection and amplification. After three selection cycles, the RNA was cloned at the cDNA level via EcoRI and BamHI into pGEM3-Zf(-), resulting in 25 clones. Two of these clones were called pGEM3-Zf(-)_PPP-I and pGEM3-Zf(-)_Ctrl-I.

The sequence of the individual RNAs at the cDNA level was determined by dideoxy sequencing.

To produce the RNAs PPP-I (112-mer; SEQ ID No. 2) and Ctrl-I (112-mer; SEQ ID No. 4), the cDNAs were amplified with the PCR primers I and II, and the amplified cDNA was transcribed in vitro with T7-RNA polymerase. The RNA radiolabeled with [5'-γ-$^{32}$P-ATP] was purified in a known manner (Weiss et al., 1997).

Example 2

Effect of the PPP-I Amptamer on the Production of PrP in Scrapie-Infected Neuroblastoma Cells [$ScN_2a$ (MHM-2)]

The cDNA coding for the PPP-I aptamer and the recPrP-I aptamer (=pGEM3-Zf(-)-Ap 1, Weiss et al., 1997) was excised from the plasmid pGEM3-Zf(-)—PPP-I and pGEM3-Zf(-)-rec PrP-I by EcoRI (5') and XbaI (3') and subcloned into pCIneo (Pharmingen). The correct sequence of the plasmid DNAs obtained thereby, pCIneo_PPP-I (corresponds to pCIneo_SAF-I deposited on Mar. 29, 1999, DSM 12753)) and pCIneo_recPrP-I was confirmed by dideoxy sequencing. Scrapie-infected neuroblastoma cells (Scott et al., 1992; $ScN_2A$, which contains the construct MHM-2 (a mouse/hamster/mouse chimera); this [$ScN_2A$ (MHM-2)] cell line was provided by Prof. S. B. Prusiner) (cells cultured to 80-100% confluence) were transfected with Lipofectamine with the plasmids pCIneo, pCIneo_PPP-I and pCIneo_recPrP-I. 48 hours after the transfection, the cells were harvested, lysed and incubated with 20 ng/µl of proteinase K (Roche Diagnostics) at 37° C. for 30 min.

The reaction was stopped with 1 mM Pefabloc, and the protein was precipitated with 5 vol. of methanol at –70° C. for 1 h. The protein was then pelleted by centrifugation at 14 000 rpm (Eppendorf bench centrifuge) for 20 minutes and subsequently resuspended in 35 µl of double-distilled water. Then 35 µl of SDS sample buffer were added. The total protein was subsequently analyzed by Western blotting, developing with the 3F4 antibody.

The advantage of this $ScN_2A$ cell line, which contains the MHM-2 construct, is that the 3F4 antibody which recognizes hamster PrP but not mouse PrP can be used in order to be able to discriminate between the transgenically expressed hamster PrP and the endogenous mouse PrP.

At the same time as the cells which were transfected with pCIneo (mock, lane 1), pCIneo_PPP-I (lane 2) and pCIneo recPrP-I (lane 3) were analyzed for synthesis of $PrP^{Sc}$ levels, the total cellular RNA was extracted with a peqGOLD RNA Pure™ Kit (PeqLab, Germany). This preparation of DNA-free and protein-free RNA was followed by reverse transcription of the RNA with the PCR primer I, and then the cDNA was amplified using PCR primers I and II. 5% by volume of the resulting DNA were analyzed on a 2.5% agarose gel which contains 1×TBE and 1 µg/ml ethidium bromide.

Example 3

Western and North-Western Blot Analyses

Brain homogenates (20% in a glucose solution) with and without treatment with 50 µg/ml pK were, after clarification by sonication, loaded onto either denaturing SDS-12% PAA gels or native polyacrylamide gels. For the clarification, 20% strength brain homogenates (in isotonic glucose solution) were diluted 1:1 in 2× dilution buffer (1× dilution buffer=1×PBS, 0.5% DOC, 0.5% NP40, 200 µM Pefablock and 1 mM PMSF). The brain homogenates were then sonicated in a Branson beaker Sonifier with 40 pulses, intensity 5, time cycle 30%. Centrifugation (15 000 min$^{-1}$ for 7 min in an Eppendorf bench centrifuge) resulted in supernatant 1, and the pellet was resuspended in 1× dilution buffer indicated above and then sonicated with 40 pulses, intensity 6, time cycle 40%. After the centrifugation described above, supernatants 1 and 2 were combined, resulting in a clear brain homogenate (5% glucose).

This material was loaded onto PAA, TBE-buffered gradient gels, usually 3.5 to 12; preferably 4 to 12 and, in particular, 6 to 12% PAA. After electroblotting on nitrocellulose, the protein bands were detected either by incubation with a radiolabeled RNA molecule and subsequent autoradiography or by incubation with PrP-specific antibody (secondary antibody: in each case POD-conjugated anti-mouse IgG or anti-rabbit IgG) and subsequent chemiluminescence.

Example 4

Models of the RNA secondary structure

Figure 2A:
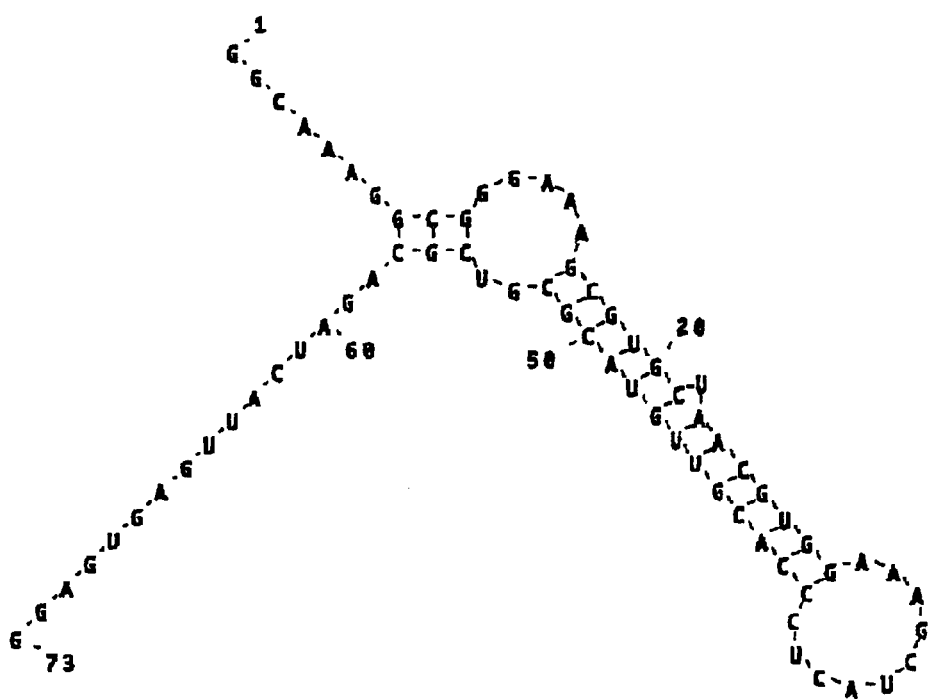
FIG. 2a shows a two-dimensional model of a stem-loop structure, constructed from the 73-mer aptamer PPP-I (SEQ ID No. 1).
Figure 2B:
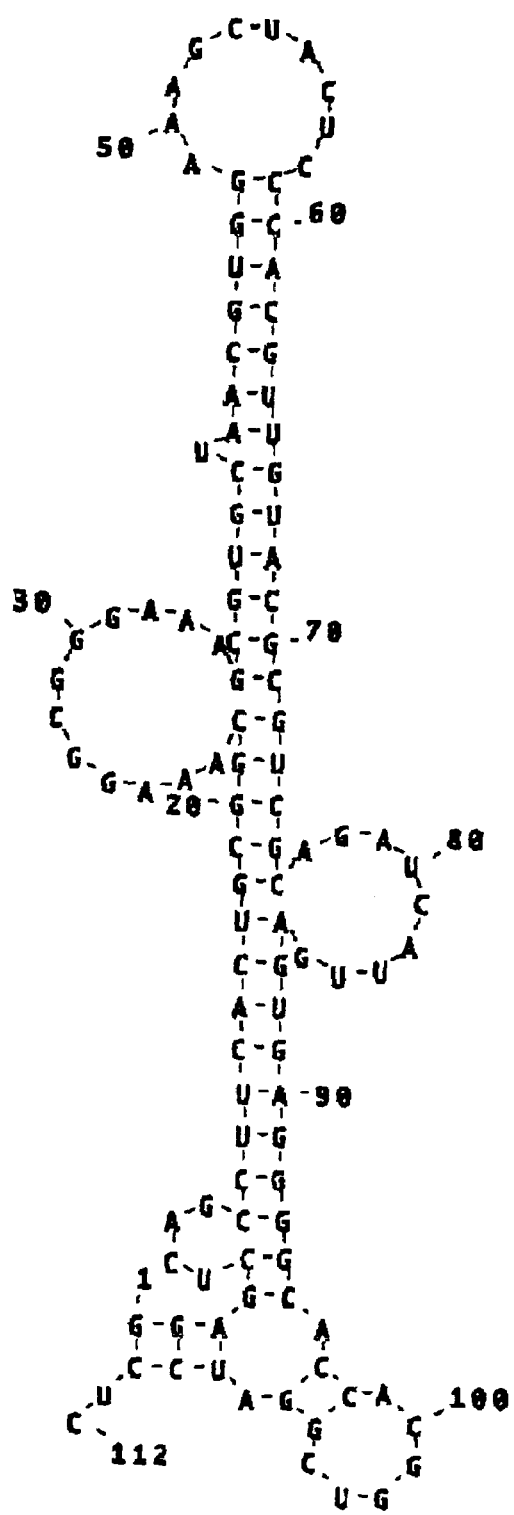
FIG. 2b shows a two-dimensional model of a stem-loop structure, constructed from the 112-mer aptamer PPP-I with the fixed regions at the 5' and 3' termini (SEQ ID No. 2).
Figure 3:
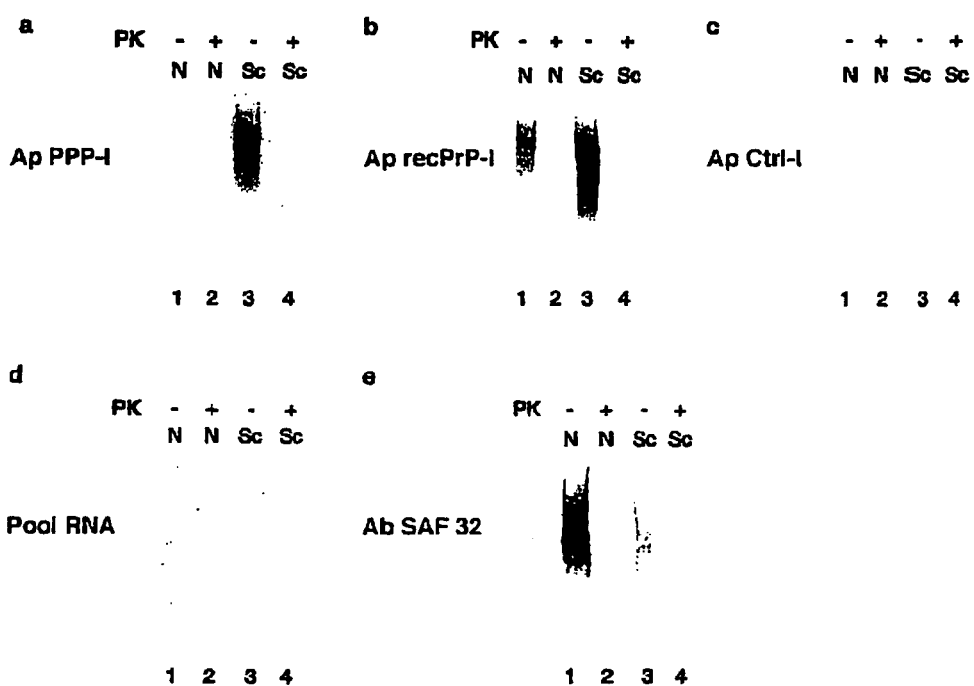
FIG. 3 shows the North-Western and Western blot analyses of brain homogenates from uninfected hamsters and hamsters suffering from scrapie with PPP-I aptamer (112-mer, SEQ ID No. 2), recPrP-I aptamer (cf. RNA aptamer motif I (Ap 1) in Weiss et al., 1997), control aptamer Ctrl-I (112-mer, SEQ ID No. 4), the pool RNA and the antibody SAF32 under native conditions. Brain homogenates from uninfected hamsters without (lanes 1) and with pK (lanes 2) and brain homogenates from hamsters suffering from scrapie without (lanes 3) and with pK (lanes 4) were fractionated on native PAA gradient gels, 4-12%, blotted and developed with radiolabeled PPP-I aptamer (112-mer, SEQ ID No. 2) (a), recPrP-I aptamer (6) (b), control aptamer Ctrl-I (112-mer, SEQ ID No. 4) (c), the radiolabeled pool RNA (d) and the antibody SAF 32 (e). It emerges that only with the PPP-I aptamer is there found to be selective binding to native $PrP^{Sc}$ from brain homogenates from hamsters suffering from scrapie without pK treatment (a, lanes 3).
Figure 4:
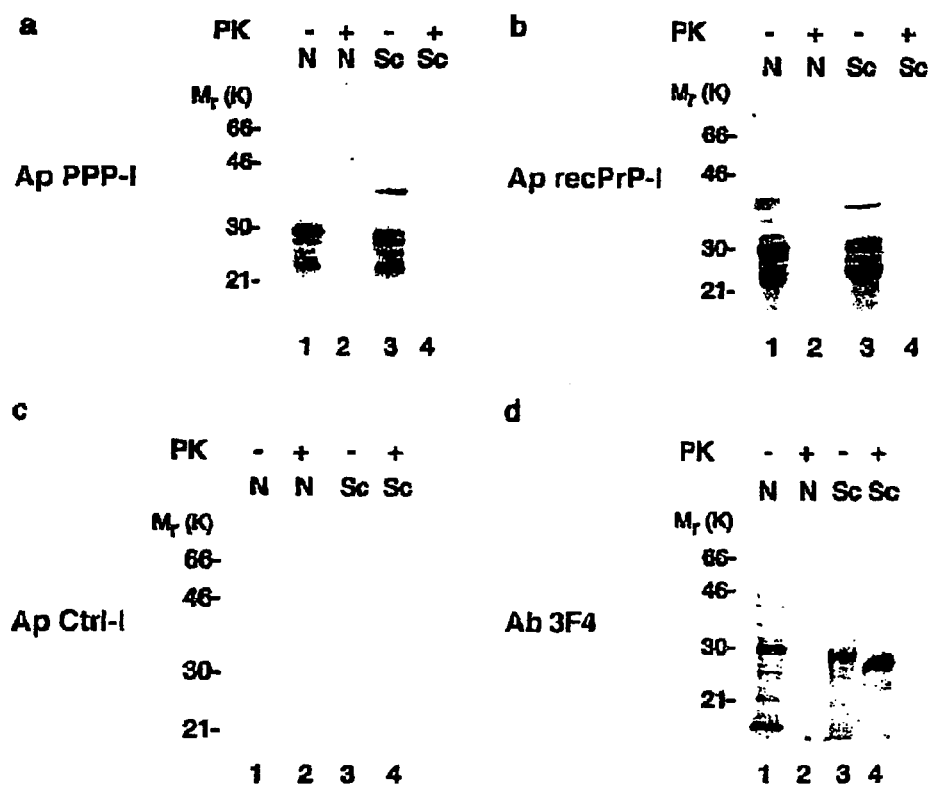
FIG. 4 shows the North-Western and Western blot analyses of brain homogenates from uninfected hamsters and hamsters suffering from scrapie with radiolabeled PPP-I aptamer (112-mer, SEQ ID No. 2), recPrP-I aptamer (cf. Weiss et al., 1997), control aptamer Ctrl-I (112-mer, SEQ ID No. 4) and the antibody 3F4 under denaturing conditions. Brain homogenates from uninfected hamsters without (lanes 1) and with pK (lanes 2) and brain homogenates from hamsters suffering from scrapie without (lanes 3) and with pK (lanes 4) were fractionated on SDS-12% PAA gels, blotted and developed with radiolabeled PPP-I aptamer (112-mer, SEQ ID No. 2) (a), recPrP-I aptamer (b), control aptamer Ctrl-I (112-mer, SEQ ID No. 4) (c) and the antibody 3F4 (d). It emerges that under denaturing conditions the PPP-I aptamer (112-mer, SEQ ID No. 2) and the recPrP-I aptamer (112-mer, SEQ ID No. 4) bind comparably well to $PrP^c$ and $PrP^{Sc}$ from brain homogenates from healthy hamsters and hamsters suffering from scrapie (a,b, lanes 3).
Figure 5:
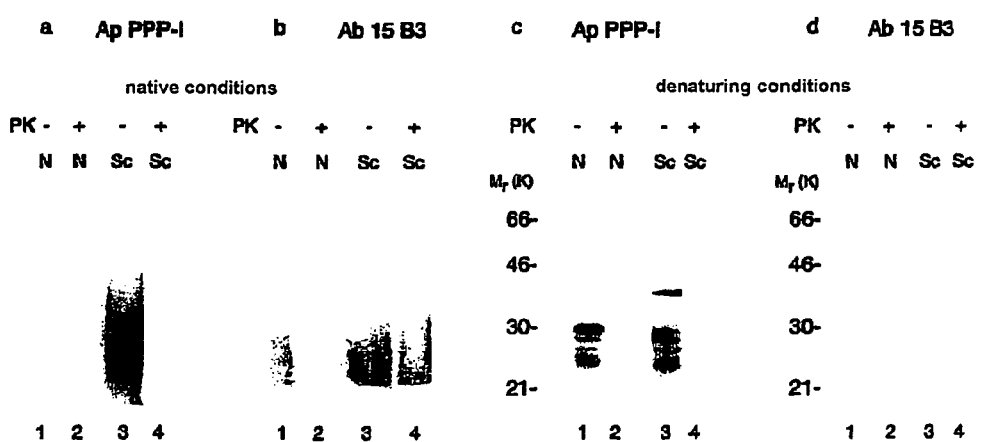
FIG. 5 shows a comparison of the PPP-I aptamer (112-mer; SEQ ID No. 2) with the antibody 15 B3 (Korth et al., 1997) in relation to the ability to bind to $PrP^c$, $PrP^{Sc}$ and PrP27-30 under native and denaturing conditions by North-Western and Western blot analyses. Brain homogenates from uninfected hamsters without (lanes 1) and with pK (lanes 2) and brain homogenates from hamsters suffering from scrapie without (lanes 3) and with pK (lanes 4) were fractionated on native PAA gradient gels, 3.5-12% (a,b) and SDS-12% PAA gels (c,d) and developed with the radiolabeled PPP-I aptamer (112-mer, SEQ ID No. 2) (a,c) and the antibody 15 B3 (b,d). It emerges that under native conditions the PPP-I aptamer binds selectively to $PrP^{Sc}$ from brain homogenates from hamsters suffering from scrapie (a, lane 3), whereas the 15B3 antibody recognizes native $PrP^c$ (b, lane 1), $PrP^{Sc}$ (b, lane 3) and PrP 27-30 (b, lane 4). The 15B3 antibody recognizes, as described (Korth et al., 1997), neither $PrP^c$, $PrP^{Sc}$ nor PrP 27-30 under denaturing conditions (d, lanes 1-4), whereas the PPP-I aptamer under denaturing conditions recognizes $PrP^c$ (c, lane 1) and $PrP^{Sc}$ (c, lane 3).
Figure 6:
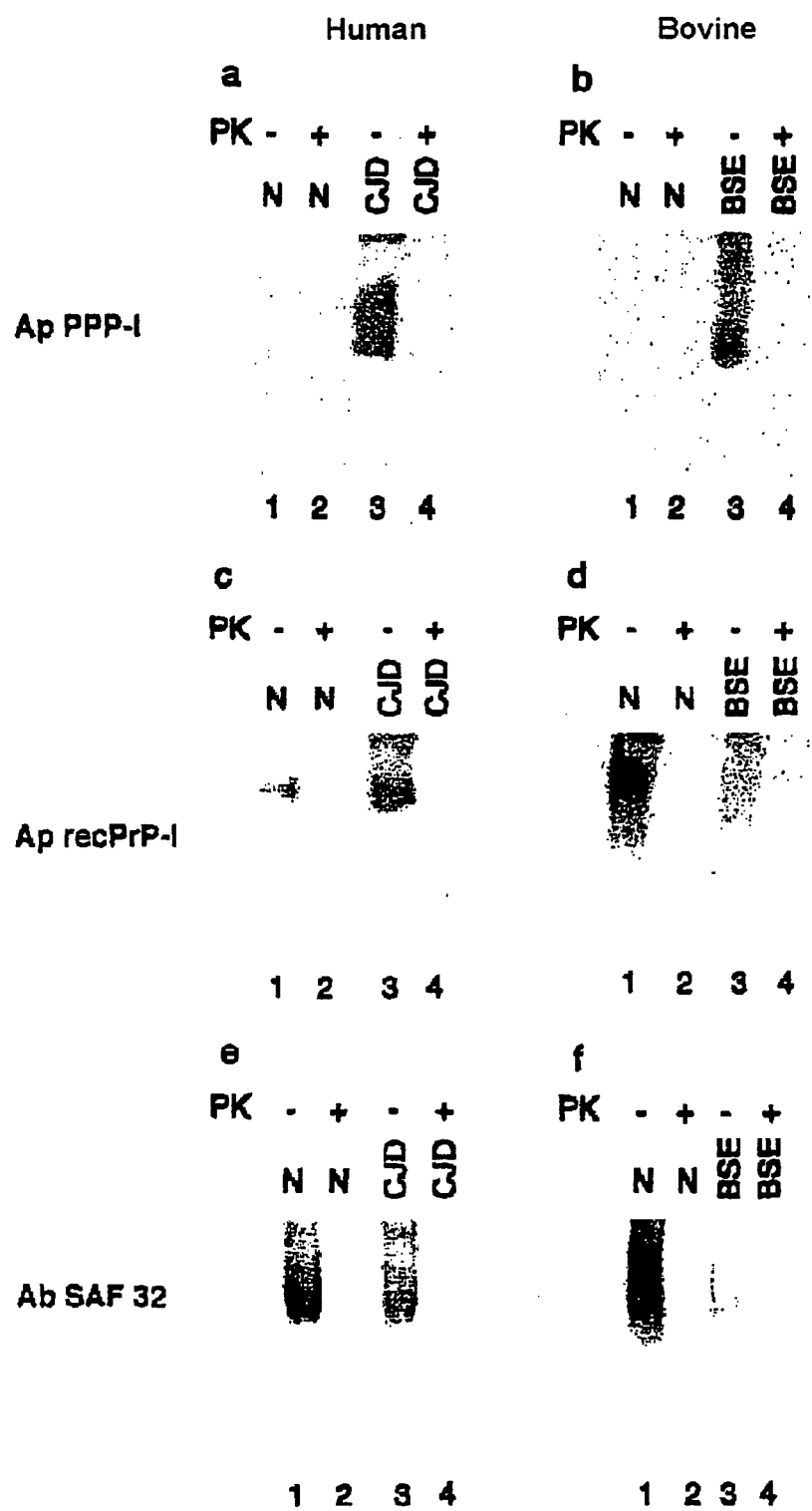
FIG. 6 shows the North-Western and Western blot analyses of brain homogenates from humans, CJD patients, cows and cattle suffering from BSE. Brain homogenates from humans without (lanes 1) and with pK (lanes 2) and brain homogenates from CJD patients without (lanes 3) and with pK (lanes 4) were fractionated on native PAA gradient gels, 4-12%, blotted and developed with radiolabeled PPP-I aptamer (112-mer, SEQ ID No. 2) (a), recPrP-I aptamer (c) (Weiss et al., 1997) and the antibody SAF 32 (e). Brain homogenates from cows without (lanes 1) and with pK (lanes 2) and brain homogenates from cattle suffering from BSE without (lanes 3) and with pK (lanes 4) were separated on native PAA gradient gels, 4-12%, blotted and developed with radiolabeled PPP-I aptamer (112-mer, SEQ ID No. 2) (b), recPrP-I aptamer (d) and the antibody SAF 32 (f). It emerges that the PPP-I aptamer selectively binds to native $PrP^{CJD/BSE}$ from brain homogenates from CJD patients and cattle suffering from BSE (a, b, lanes 3).
Figure 7:
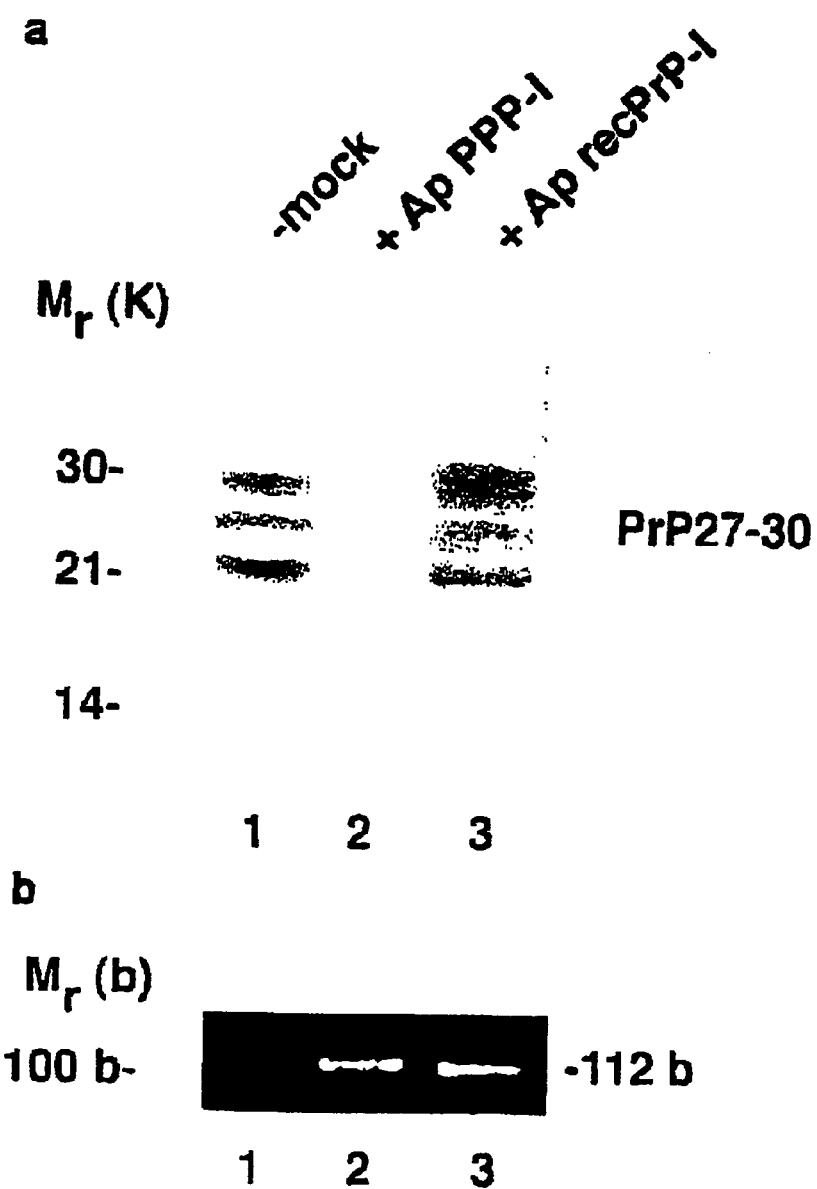
FIG. 7 shows a Western blot and RT-PCR analysis of protein and RNA preparations from scrapie-infected neuroblastoma cells [$ScN_2a$ (MHM-2)], which have been transfected with plasmids which encode the aptamers PPP-I and recPrP-I. (a) The protein preparations from scrapie-infected neuroblastoma cells transfected with pCIneo (mock, lane 1), pCIneo_PPP-I (lane 2) and pCIneo_recPrP-I (lane 3) were, after the treatment with pK, analyzed on an SDS-12% PAA gel, blotted on nitrocellulose and developed with the PrP-specific antibody 3F4. (b) RNA was extracted from [$ScN_2a$ (MHM-2)] cells transfected as described under (a), and subjected to an RT-PCR reaction using PCR primers I and II. The resulting DNA was analyzed on a 2.5% agarose gel. It emerges that in the presence of the PPP-I aptamer there is no longer an $PrP^{Sc}$ synthesis (a, b, lanes 2), whereas the presence of the rec PrP-I aptamer has no effect on the synthesis of $PrP^{Sc}$ (a, b, lanes 3)

The models of the secondary structure of the PPP-I aptamer 73-mer; SEQ ID No. 1, 112-mer,; SEQ ID No. 2 were produced with the software program MacDNASIS Pro V1.0 (cf. FIGS. 2a + 2b).

The sequences of PPP-I (SEQ ID Nos: 1 and 2) and the control aptamer Ctrl-I (SEQ ID Nos: 3 and 4) are indicated in the following sequence listing.

LIST OF REFERENCES

Demainay R. et al., Late Treatment with Polene Antibiotics can prolong the Survival of scrapie-affected Animals. J. Virol. 71 (1997), 9685-9689.

Famulok, M.: Molecular Recognition of Amino Acids by RNA-Aptamers: An L-Citrulline Bindung Motif and its Evolution into an L-Arginine Binder. J. Am. Chem. Soc. 116 (1994), 1698-1706

Gerhart E., Wagner H., Brantl S.: Kissing and RNA stability in antisense Control of Plasmid Replication. Trends Biochem. Sci. (December 1998), 23 (12): 451-454

Korth C., Stierli B., Streit P., Moser M., Schaller O., Fischer R., Schulz-Schaeffer W., Kretzschmer H., Raeber A., Braun U., Ehrensperger F., Hornemann S., Glockshuber R., Riek R., Billeter M., Wuthrich K., Oesch B.: Prion (PrP$^{Sc}$)-specific epitope defined by a monoclonal antibody. Nature, 390, 74-77 (1997)

King D. J., et al., Novel Combinatorial Selection of Phosphorothioate Oligonucleotide Aptamers. Biochemistry, 37 (1998), 16489-16493.

Kumar M., Carmichael G. G.: Antisense RNA: Function and Fate of Duplex RNA in Cells of higher Eukaryotes. Microbiol. Mol. Bio. 1 Rev. (December 1998), 62 (4): 1415-1434

Lasmézas C. I. et al., Transmission of the BSE Agent to Mice in the Absence of Detectable abnormal Prion Protein. Science 275, 404-405 (1997).

Lasmézas C.I. and Weiss S.: Molecular Biology of Prion Diseases. In: Cary J. W, Linz J. E., Bhatnagar D., eds. Microbial food-borne disease: mechanisms of patho-genesis and toxin synthesis. Lancaster: Technomic Publishing Company, 1999 (in press).

Prusiner, S. B., Scott M. R., DeArmond S. J., and Cohen F. E.: Prion protein biology. Cell, 99, 337-348 (1998).

Rieger R., Lasmézas C. I., Weiss S.: Role of the 37 kDa laminin receptor precursor in the life cycle of prions. Transfus. Clin. Biol., 6, 7-16, 1999.

Scott, M. R., Kohler, R., Foster, D., Prusiner, S. B.: Chimeric prion protein expression in cultured cells and transgenic mice. Protein Science, 1, (1992), 986-997.

Tuerk, C. and Gold, L.: Systematic evolution of ligands by exponential enrichment; RNA ligands to bacteriophage T4 DNA polymerase. Science (1990), 249, 505-510.

Vanhee-Brossollet C., Vaquero C.: Do Natural Antisense Transcripts Make Sense in Eukaryotes. Gene (1998), 221 (1): 1-9

Weiss S., Proske D., Neumann M., Groschup M., Kretzschmar H., Famulok M. and Winnacker L.: RNA Aptamers Specifically Interact with the Prion Protein PrP. J. Virol. 71 (1997), 8790-8797.

Weissmann C., and Aguzzi A: Bovine spongiform encephalophathy and early onset of varient Creutzfeld-Jakob disease. Curr. Opin. Neurobiol. 7, 695-700 (1997)

The sequence listing attached hereto and set forth separately on the computer diskette is hereby incorporated by reference.

The invention claimed is:

1. A nucleic acid molecule comprising:

[SEQ ID NO: 1]

5'ggcaaaggcg ggaaagcgug cuaacgugga aagcuacucc cacguuguac gcgucgcaga ucauugagug agg3', or

[SEQ ID NO: 2]

5'ggagcucagc cuucacugcg gcaaaggcgg gaaagcgugc uaacguggaa agcuacuccc acguuguacg cgucgcagau cauugaguga ggggcaccac ggucggaucc uc3'.

2. A composition comprising a nucleic acid molecule according to claim 1 and a pharmaceutically acceptable carrier and/or excipient.

* * * * *